United States Patent
Gojny

(10) Patent No.: US 6,787,159 B2
(45) Date of Patent: Sep. 7, 2004

(54) PROCESS FOR THE PREPARATION OF A COSMETIC EXTRACT FROM MARINE OOZE

(75) Inventor: Paul Gojny, Cuxhaven (DE)

(73) Assignee: La Mer Cosmetics AG, Cuxhaven (DE)

(*) Notice: Subject to any disclaimer, the term of this patent is extended or adjusted under 35 U.S.C. 154(b) by 0 days.

(21) Appl. No.: 10/169,688

(22) PCT Filed: Jan. 3, 2001

(86) PCT No.: PCT/EP01/00020
§ 371 (c)(1),
(2), (4) Date: Sep. 3, 2002

(87) PCT Pub. No.: WO01/49254
PCT Pub. Date: Jul. 12, 2001

(65) Prior Publication Data
US 2003/0049288 A1 Mar. 13, 2003

(51) Int. Cl.[7] .................. A61K 35/24; A61K 35/12; A61K 35/64; A61K 35/32; A61K 35/78
(52) U.S. Cl. ............... 424/543; 424/725; 424/520; 424/538; 424/549
(58) Field of Search ................ 424/543, 195.1, 424/725, 520, 538, 549

(56) References Cited

FOREIGN PATENT DOCUMENTS

| CH | 286 680 | 10/1952 |
|---|---|---|
| DE | 2 461 161 | 6/1976 |
| DE | 3 113 287 | 10/1982 |
| DE | 3 221 502 | 12/1983 |
| DE | 299 19 044 | 10/1999 |
| JP | 11228344 | 8/1999 |
| RU | 2043100 | 9/1995 |
| RU | 2073999 | 2/1997 |
| RU | 2107504 | 3/1998 |
| WO | 00 40255 | 7/2000 |

*Primary Examiner*—Patricia Leith
(74) *Attorney, Agent, or Firm*—Vidas, Arrett & Steinkraus PA

(57) ABSTRACT

The invention relates to a process for the preparation of extracts from marine ooze. To extract a larger proportion of the cosmetically and balneologically active ingredients from the ooze, the process proposes paraffinum subliquidum, ethanol, dimethicone a water/ethanol mixture and a mixture of water/ethanol/glycerin/propylene glycol. The mixture is extracted while stirring it either for 24 to 30 hours at room temperature or 1 to 3 hours at 50° to 70° C. and is filtered. The filtrate has a proportion of active ingredients from the marine ooze.

6 Claims, No Drawings

PROCESS FOR THE PREPARATION OF A COSMETIC EXTRACT FROM MARINE OOZE

FIELD OF THE INVENTION

The invention relates to a process for the preparation of a cosmetically usable extract from marine ooze and a product including an extract from marine ooze, and its use.

BACKGROUND OF THE INVENTION

Organ extracts and plant extracts have been popular additives and, if experts feel, efficient additives for years, specifically for cosmetic products of very different types. It is known to employ balneological packs and facial masks on the basis of marine ooze. Superior-value products such as cosmetic creams, lotions, and cosmetic liquids could not be prepared because of the high insoluble proportions in the marine ooze.

A process for the preparation of an extract from German Sea ooze is known from the German Patent 31 13 287. The disadvantage of this process is that it incorporates only some part of the efficient ingredients of the German Sea ooze and, therefore, is only of a limited efficiency. Also, the process involves comparatively high expenditure in implementing it.

A cosmetic creme facial mask including marine ooze and a process for its preparation has been known from DE 3 221 502 A1. The cosmetic creme facial mask contains 10–40% of dried marine ooze. Both an oil-in-water creme and a water-in-oil creme may be used as a basis of the creme. The marine ooze is selected in such a way that mineral particles 50–100 $\mu$m in size are contained. To prepare the creme facial mask, the dry ooze is added to the emulsion when still hot after the creme basis is emulsified and, subsequently, the emulsion is stirred when cold. The facial mask serves for care and massage. At the same time, a cosmetic effect makes itself felt because of the ooze ingredients fed in by the dry ooze.

BRIEF SUMMARY OF THE INVENTION

It is the object of the invention to provide an extract from marine ooze and a process for the preparation of a cosmetically used extract from marine ooze which achieves substantially better yields and is implementable at a lower expenditure.

DETAILED DESCRIPTION OF INVENTION

The surprising result was that one of the following formulation examples allows one to simultaneously extract both the water soluble constituents of the marine ooze and the other ones which both are particular important for a cosmetic effect:

| Formulation example 1 | |
|---|---|
| Paraffinum subliquidum | 100 parts by weight |
| Dried pulverulent ooze | 50 parts by weight |

| Formulation example 2 | |
|---|---|
| Ethanol | 100 parts by weight |
| Dried pulverulent ooze | 50 parts by weight |

| Formulation example 3 | |
|---|---|
| Dimethicone (silicone oil) | 100 parts by weight |
| Dried pulverulent ooze | 50 parts by weight |

| Formulation example 4 | |
|---|---|
| Water | 80 parts by weight |
| Ethanol | 20 parts by weight |
| Dried pulverulent ooze | 50 parts by weight |

According to the invention, the above-mentioned extractant is mixed with comminuted ooze. The mixture is extracted by stirring the constituents for 1 to 3 hours at 50 to 70° C. Alternatively, the mixture may also be stirred for 24 to 30 hours at room temperature. The mixture is filtered subsequently.

Another formulation example which is particularly preferred replaces the weight proportions indicated for water in formulation example 4 with a mixture of water, glycerin, and propylene glycol.

| Formulation example 4b | |
|---|---|
| Water | 5–15 parts by weight |
| Glycerin | 35–40 parts by weight |
| Propylene glycol | 25–30 parts by weight |
| Ethanol | 15–25 parts by weight |
| Dried pulverulent ooze | 45–55 parts by weight |

The mixture thus prepared from an extractant and pulverulent ooze is stirred for 1 to 3 hours at 50 to 70° C. and is filtered subsequently. The extract obtained after filtration is of a yellowish color which makes it possible to process it particularly well in a neutral color in other products.

Preferably, the ratio between the dried pulverulent ooze and the extractant is about 1:2 by weight. This mixing ratio ensures that the constituents contained in the ooze are reliably extracted.

In a preferred continuation of the process for formulation example 4b, the pulverulent ooze is weighed out and water is added thereto while stirring, in a first step. The addition of propylene glycol and glycerin is effected subsequently with the suspension being stirred for about 1 hour while being slowly heated up to about 60° C. The mixture cools down to room temperature subsequently. Ethanol is added afterwards and the suspensions is stirred for about 2 hours.

Preferably, the ooze extract thus obtained rests for about 24 hours, which achieves a separation of the solid phase and the liquid phase. The process thus carried out for the preparation of an extract from ooze can be implemented rapidly and at a low cost.

Preferably, the ooze extract is roughly filtered first and is finely filtered subsequently for its filtration. Filter paper, particularly cellulose filter paper, is preferably used for fine filtration.

The inventive object is also attained by a product for cosmetic application which includes an extract from ooze, specifically marine ooze, in which the efficient substances of the ooze are extracted according to the above process.

The marine ooze extract prepared according to the inventive process is suited particularly well for being used in cosmetic products of very different types. In particular, the extract may be used in a pure form or as a proportion of conventional cosmetic products. Using it in case of problematic skin conditions is particularly advantageous.

Dermatological tests have shown that if the extract thus obtained from ooze is used it will result in a significant improvement in the skin moisture of human beings. Test series have shown that if a preparation including an extract from marine ooze is used in the lower-arm area over a period of 4 weeks a pronounced improvement is reached in skin moisture.

The application example below is intended to elucidate the details of the inventive process in more detail.

The material to start from is marine ooze which is used in the following approximate composition of its mineral constituents:

24 to 56% sand, 70 to 90% silt, 10 to 22% clay.

An ooze of this composition is referred to as "sandy ooze". Apart from the mineral constituents, the sandy ooze has a multitude of macroscopically perceivable living beings such as sandworms, cockles, tellins, and scrobicularia.

This marine ooze and, hence, the living beings contained therein are comminuted and are blended with an extractant mixture according to one of the above-indicated formulation examples. In a first preparation process, the constituents are stirred for 1 to three hours at 50 to 70° C. and are filtered subsequently. The filtrate, prior to its use in cosmetic products, is filled into aluminum bottles and is kept in a refrigerator.

In a second preparation example, the mixed constituents are stirred for 24 to 30 hours at room temperature. Filtration is done subsequently and the filtrate, prior to its use in cosmetic products, is filled into aluminum bottles and is kept in a refrigerator.

The present invention provides the possibility to incorporate the organic, cosmetically active substances of the marine ooze also in high-quality cosmetic products. The above-mentioned extractants are also suited for use in other natural mixtures of biological breakdown products.

What is claimed is:

1. A process for the preparation of a cosmetically usable extract from marine ooze, characterized in that;
    a) dried, pulverulent marine ooze is mixed with an extractant of about 10 parts by weight of water, 40 parts by weight of glycerin, 30 parts by weight of propylene glycol and 20 parts by weight of ethanol to form a mixture,
    b) stirring the mixture from part (a) for 1 to 2 hours at 50° C. to 70° C., and
    c) filtering to recover a cosmetically usable extract.

2. A process for the preparation of a cosmetically usable extract from marine ooze characterized in that;
    a) dried, pulverulent marine ooze is weighed,
    b) water is added to the weighed pulverulent marine ooze to form a mixture,
    c) the mixture from part (b) is stirred,
    d) propylene glycerol and glycerin are added to the stirred mixture from part (c) to form a second mixture,
    e) said second mixture from part (d) is stirred for about 1 hour while heating to about 60° C. to form a heated mixture,
    f) cooling said heated mixture from part (e) to room temperature to form a cooled mixture,
    g) adding ethanol to the cooled mixture of part (f),
    h) stirring for about 2 hours, and
    i) filtering to recover a cosmetically usable extract.

3. The process as claimed in claim 2, characterized in that the mixture of step b) of claim 2 is allowed to rest for about 24 hours, which achieves a separation of the solid phase and the liquid phase before the filtering step.

4. The process of claim 3, wherein filtering comprises rough filtration followed by fine filtration.

5. The process as claimed in claim 4, characterized in that cellulose filter paper is used for fine filtration.

6. The process as claimed in claim 2, characterized in that the ratio of the dried pulverulent ooze and the extractant is approximately 1:2 by weight.

* * * * *